United States Patent
Rossi

(10) Patent No.: US 11,266,849 B2
(45) Date of Patent: Mar. 8, 2022

(54) CONTROL DEVICE AND A MACHINE FOR INTERACTIVE CEREBRAL AND BODILY NAVIGATION WITH REAL-TIME ANATOMICAL DISPLAY AND CONTROL FUNCTIONS

(71) Applicant: EB NEURO S.P.A., Florence (IT)

(72) Inventor: Marco Rossi, Verona (IT)

(73) Assignee: EB NEURO S.P.A., Florence (IT)

( * ) Notice: Subject to any disclaimer, the term of this patent is extended or adjusted under 35 U.S.C. 154(b) by 0 days.

(21) Appl. No.: 16/215,895

(22) Filed: Dec. 11, 2018

(65) Prior Publication Data
US 2019/0175931 A1  Jun. 13, 2019

(30) Foreign Application Priority Data

Dec. 12, 2017 (IT) .......................... 102017000142893

(51) Int. Cl.
*A61N 2/00* (2006.01)
*A61B 5/00* (2006.01)
(Continued)

(52) U.S. Cl.
CPC .............. *A61N 2/006* (2013.01); *A61B 5/742* (2013.01); *A61B 5/7455* (2013.01); *A61B 34/20* (2016.02);
(Continued)

(58) Field of Classification Search
CPC .................. A61B 5/062; A61B 5/7455; A61B 2034/2074; A61B 5/0484; A61B 5/04001;
(Continued)

(56) References Cited

U.S. PATENT DOCUMENTS

2004/0111127 A1* 6/2004 Gliner ................ A61N 1/36178
607/45
2007/0179558 A1* 8/2007 Gliner ................ A61N 1/36082
607/45

(Continued)

OTHER PUBLICATIONS

Mehroosh Sidiq et al, Augmented Reality VS Virtual Reality, International Journal of Computer Science and Mobile Computing, vol. 6 Issue.6, Jun. 2017, p. 324-327 (Year: 2017).*

(Continued)

*Primary Examiner* — Navin Natnithithadha
*Assistant Examiner* — Sunita Reddy
(74) *Attorney, Agent, or Firm* — Shuttleworth & Ingersoll, PLC; Timothy Klima

(57) ABSTRACT

A control device (1) for machines (10) for magnetic cerebral or peripheral stimulation with cerebral and bodily navigation, which includes a plurality of keys (2) which can be associated with various functions of the machine (10) and configured for activating, when pressed, a respective function of the machine (10) associated with the respective key (2). The control device (1) also includes a touch screen (3) configured for displaying anatomical information of the subject or patient for a direct viewing from the operator with information relative to the function of the machine (10) which can be activated by the keys (2) and activating at least one further function of the machine (10) associated with a respective icon (7) which can be pressed with the touch screen (3), such as, for example, a stimulation.

7 Claims, 3 Drawing Sheets

(51) Int. Cl.
*A61B 34/20* (2016.01)
*A61N 2/02* (2006.01)
*A61B 5/06* (2006.01)
*A61B 5/24* (2021.01)
*A61B 5/377* (2021.01)

(52) U.S. Cl.
CPC ............... *A61N 2/02* (2013.01); *A61B 5/062* (2013.01); *A61B 5/24* (2021.01); *A61B 5/377* (2021.01); *A61B 5/4064* (2013.01); *A61B 5/4836* (2013.01); *A61B 2034/2074* (2016.02)

(58) Field of Classification Search
CPC ..... A61B 5/4836; A61B 5/4064; A61B 5/742; A61B 34/20; A61N 2/02; A61N 2/006
USPC ...................................................... 600/9–15
See application file for complete search history.

(56) References Cited

U.S. PATENT DOCUMENTS

| | | | | |
|---|---|---|---|---|
| 2010/0256438 A1* | 10/2010 | Mishelevich | ........... | A61N 2/006 600/13 |
| 2011/0160796 A1* | 6/2011 | Lane | ................. | A61N 1/36139 607/45 |
| 2011/0224571 A1* | 9/2011 | Pascual-Leone | .... | A61B 5/0484 600/544 |
| 2012/0197163 A1* | 8/2012 | Mishelevich | ............ | A61N 7/00 601/2 |
| 2013/0131754 A1* | 5/2013 | Sarvazyan | ......... | A61N 1/37217 607/45 |
| 2013/0281890 A1* | 10/2013 | Mishelevich | .......... | A61N 1/361 601/2 |
| 2013/0289385 A1* | 10/2013 | Lozano | .................. | A61B 5/055 600/411 |
| 2014/0031605 A1* | 1/2014 | Schneider | .............. | A61N 2/006 600/14 |
| 2014/0058189 A1* | 2/2014 | Stubbeman | ........... | A61N 2/006 600/13 |
| 2015/0119689 A1* | 4/2015 | Pascual-Leone | ...... | A61B 5/055 600/410 |
| 2015/0302639 A1* | 10/2015 | Malekian | ................ | H04L 67/42 345/420 |
| 2016/0008620 A1* | 1/2016 | Stubbeman | ........ | A61N 1/36082 600/14 |
| 2017/0151436 A1* | 6/2017 | Flaherty | ................... | A61N 7/00 |
| 2017/0365101 A1* | 12/2017 | Samec | ..................... | A61B 3/09 |
| 2019/0011703 A1* | 1/2019 | Robaina | .................. | G06F 3/013 |

OTHER PUBLICATIONS

Mullen, T., Kothe C., Chi. M., Ojeda, A., Kerth, T., Makeig, S., Jung, T-P., Cauwenberghs, G. (2015). Real-time Neuroimaging and Cognitive Monitoring Using Wearable Dry EEG. IEEE Transactions on Biomedical Engineering. Special Issue on Wearable Technologies. Nov. 2015;62(11):2553-67. (Year: 2015).*

First demonstration of Real-Time Brain Mapping in a Web Browser. Intheon, Apr. 10, 2016. (Year: 2016).*

TMS Neuronavigation Visor2 User Guide. ANT Neuro B.V./ eemagine Medical Imaging Solutions GmbH. Sep. 8, 2014. (Year: 2014).*

WO 2016/023126 published Feb. 18, 2016 (PCT/CA2015/050768 filed Aug. 13, 2015), 202 pages—English.

WO2015/153675 published Oct. 8, 2015 (PCT/US2015/023693 filed Mar. 31, 2015) 89 pages—English.

* cited by examiner

CONTROL DEVICE AND A MACHINE FOR INTERACTIVE CEREBRAL AND BODILY NAVIGATION WITH REAL-TIME ANATOMICAL DISPLAY AND CONTROL FUNCTIONS

CROSS REFERENCE TO RELATED APPLICATIONS

This application relates to, and claims priority from, IT-102017000142893 filed Dec. 12, 2017, the entire contents of which are incorporated herein by reference.

FIGURE SELECTED FOR PUBLICATION

FIG. 1

BACKGROUND OF THE INVENTION

Field of the Invention

This invention relates to a control device for machines for interactive cerebral and bodily navigation. The invention also relates to a machine for interactive cerebral and bodily navigation comprising the above-mentioned control device.

As used herein, the expression "interactive cerebral and bodily navigation" means the increased reality guidance procedures for identifying areas of the central or peripheral nervous system which allow the electrical activity of the brain to be stimulated or measured.

Description of the Related Art

There are prior art machines for guiding the operator during the cerebral or peripheral navigation phases using a monitor on which are displayed the virtual images of the subject or patient, a keyboard with mouse to perform the normal operations which can be performed with these input devices and an image acquisition/stimulation unit configured to perform the examination and obtain the sensitive data to be displayed on the screen.

In the case of transcranial magnetic stimulation and navigation examinations, the test is carried out by a doctor or by a technician and performed in various phases.

For each phase, the need is known of displaying the anatomical areas in a simple and precise manner and selecting the functions which each key must perform.

Disadvantageously, the prior art machines do not allow a virtual view of the zones represented directly from the perspective of the operator, but use a monitor and a keyboard or mouse, thus often causing an unnatural movement of the operations and an uncomfortable selection of a plurality of software functions.

In addition, the functions necessary for activating the device can change following various situations.

Alternatively, it is possible to use different keyboards as a function of the operation or the software to be executed, thus resulting in an extension of the set up times of the machine and difficulty in positioning by the operator.

Prior art machines are described in patent documents WO2015/153675 and WO2016/023126, the entire contents of each of which are incorporated herein by reference.

ASPECTS AND SUMMARY OF THE INVENTION

The technical purpose of this invention is therefore to provide a control device and a machine for magnetic cerebral or peripheral stimulation with cerebral and bodily navigation which are able to overcome the drawbacks of the prior art.

The aim of this invention is therefore to provide a control device and a machine for interactive cerebral and bodily navigation which allows the positioning of the stimulation coil to be easily controlled and the control of functions with a single operator, thus reducing the testing or setting up times.

The technical purpose indicated and the aim specified are substantially achieved by a control device and a machine for interactive cerebral and bodily navigation examinations with the technical features described in one or more of the appended claims.

Further features and advantages of the invention are more apparent in the non-limiting description which follows of a control device and a machine for interactive cerebral and bodily navigation.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
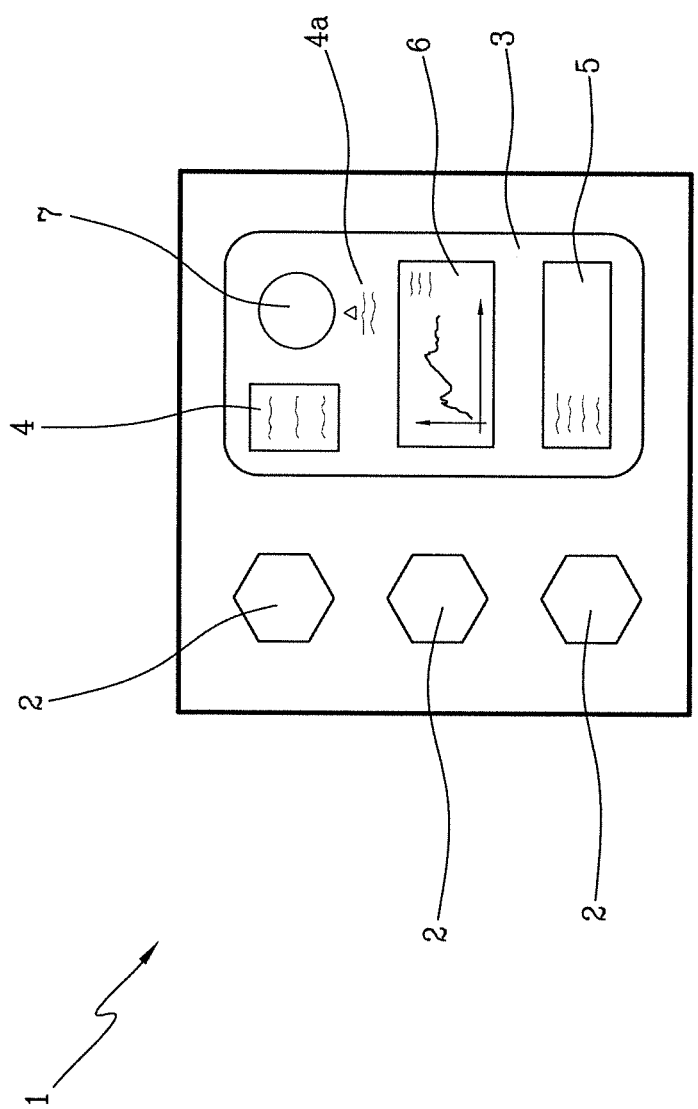
FIG. 1 is a schematic representation of an embodiment of a control device according to the invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

With reference to the accompanying drawings, the numeral 1 denotes in its entirety a device for interactive cerebral and bodily navigation, which for simplicity will be referred to hereafter as control device 1.

The control device 1, shown in FIG. 1, comprises a plurality of keys 2 which can be associated with various functions of a machine 10 for interactive cerebral and bodily navigation.

The keys 2 are configured for activating, when pressed, a respective function of the machine 10 associated with the respective key 2.

In other words, each key 2 makes it possible to activate a specific function of the machine to perform stimulations and/or analyses of various types on a patient.

For example, it is possible that the machine 10 can obtain results from an examination performed on the patient and/or operate directly on the patient and a key will therefore be necessary to activate each of these operations.

According to the invention, the device 1 also comprises at least one touch screen 3 configured for displaying information relating to the anatomical structures of the patient with the relative functions of the machine which can be activated by the keys 2.

The term "information" is used to mean any type of output or instruction relative to the function which can be activated by pressing the relative key 2.

Preferably, the touch screen 3 is configured for displaying increased reality information 3D in real time and textual information 4 on a function of the machine 10 associated with a respective key 2. Textual information 4 means displaying the name of the function which can be executed, or an icon by pressing the respective key 2 or the relative code or directly a short explanation of what the function is able to do.

Preferably, the touch screen 3 is configured to associate the functions of the machine 10 with respect to the relative key 2.

In other words, it is possible by means of menu options 5 to associate a predetermined function to one of the keys 2, before or during the operation on the basis of the needs of the doctor who must use the control device 1.

Preferably, the touch screen 3 is configured for displaying results of the examination in progress.

The term "results" means any type of output released by the machine 10 and which can be displayed on the touch screen 3, such as, for example, diagrams 6 or other types of the sensitive data for the purpose of the examination.

Preferably, the touch screen 3 is configured for personalising a display of a result of the examination in progress.

In other words, by using the menu options 5 or, for example, directly through the diagram 6 it is possible to modify the size of the diagram, the characters or their position on the touch screen 3.

Alternatively, it is possible to modify the colors with which to display the various diagrams 6 or the data obtained from the examination in such a way as to highlight a result of interest with respect to another.

Preferably, the menu options 5 allows modification of a position of the textual information 4 or, for example, a size dimension of the characters of the same.

The touch screen 3 is also configured to activate at least one further function of the machine 10 associated with a respective icon 7 which can be pressed from the touch screen 3.

In other words, it is possible to associate other functions of the machine 10, not linked to the keys 2, to one or more icons 7 which can be viewed and pressed on the touch screen 3. In this way it is possible to expand the number of functions which the control device 1 is able to activate.

Preferably, by means of the menu options 5, it is possible to modify a size or a position of the icon 7.

Preferably, just as for the keys 2, the touch screen 3 is able to display textual information 4a and/or results associated with the icon 7 or associate the functions of the machine 10 relative to the respective icon 7.

Preferably, by means of the menu options 5 (or the relative diagram 6) it is possible to personalize the display of the result of the examination in progress linked to the function activated by pressing the icon 7 or associating different functions to the icon 7.

Preferably, the control device 1 described above can be of the wireless type (but it may also be integrated in the machine 10).

Preferably, the touch screen 3 may have a capacitive, resistive or other type of screen.

Figure 2:
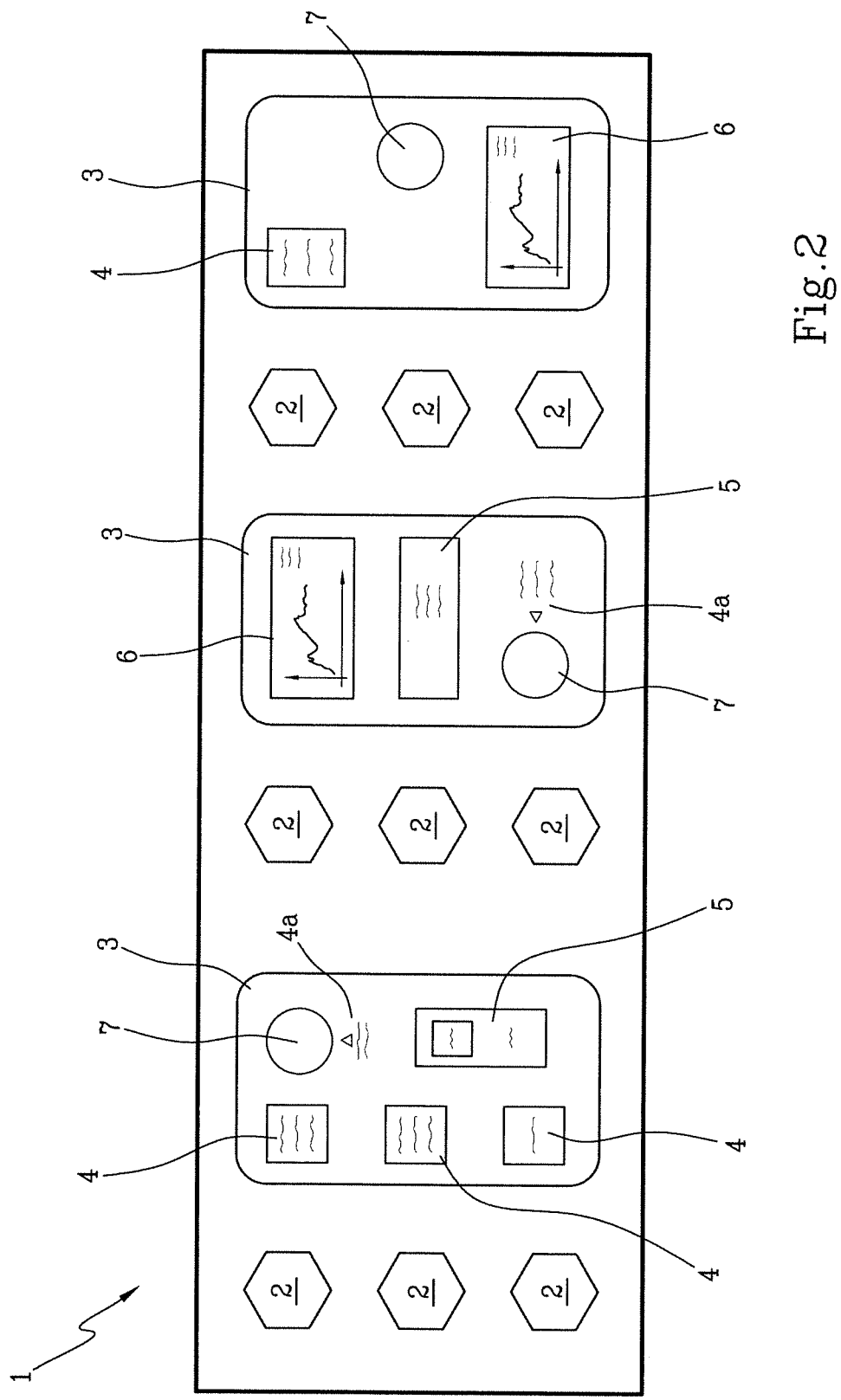
FIG. 2 is a schematic representation of a further embodiment of the control device according to the invention.

FIG. 2 shows a second embodiment of the control device 1 according to this invention which comprises a plurality of touch screens 3 (in the specific example there are three touch screens 3 but there can be only two or more).

In the example of FIG. 2, each touch screen 3 is associated with at least three keys 2 (but there can be a different number of keys 2 associated with the respective touch screen 3).

Preferably, each touch screen 3 is configured for displaying a respective result of the examination in progress. In other words, based on the results which the examination performed by the machine 10 must provide, each touch screen 3 is able to display the results separately.

Preferably, each touch screen is associated with respective keys 2 which are configured to perform a function of the machine 10 associated with the respective result. In other words, each touch screen 3 is associated and interacts only with the keys which are linked to the result displayed on the screen.

For example, it is possible that one of the touch screens 3 displays a worrying result allowing, however, the user (either the doctor or the operator) to intervene in a timely fashion by pressing one of the keys 2 whose function activates the specific function of the machine 10.

Preferably, each of the touch screens 3 is configured to act like the single touch screen 3 of the embodiment of FIG. 1, therefore being able to display results, textual information, allow different functions to be associated to the respective keys 2 or allow the displaying of the results to be personalized. Moreover, each touch screen 3 is able to activate further functions through respective icons 7 such as in the embodiment of FIG. 1.

Preferably, the control device 1 of FIG. 2 may also be of the wireless type.

In FIG. 2, the control device 1 has a set of keys 2 and touch screens 3 distributed along a line, but a different configuration of them is possible, such as, for example, in the form of a matrix.

Figure 3:
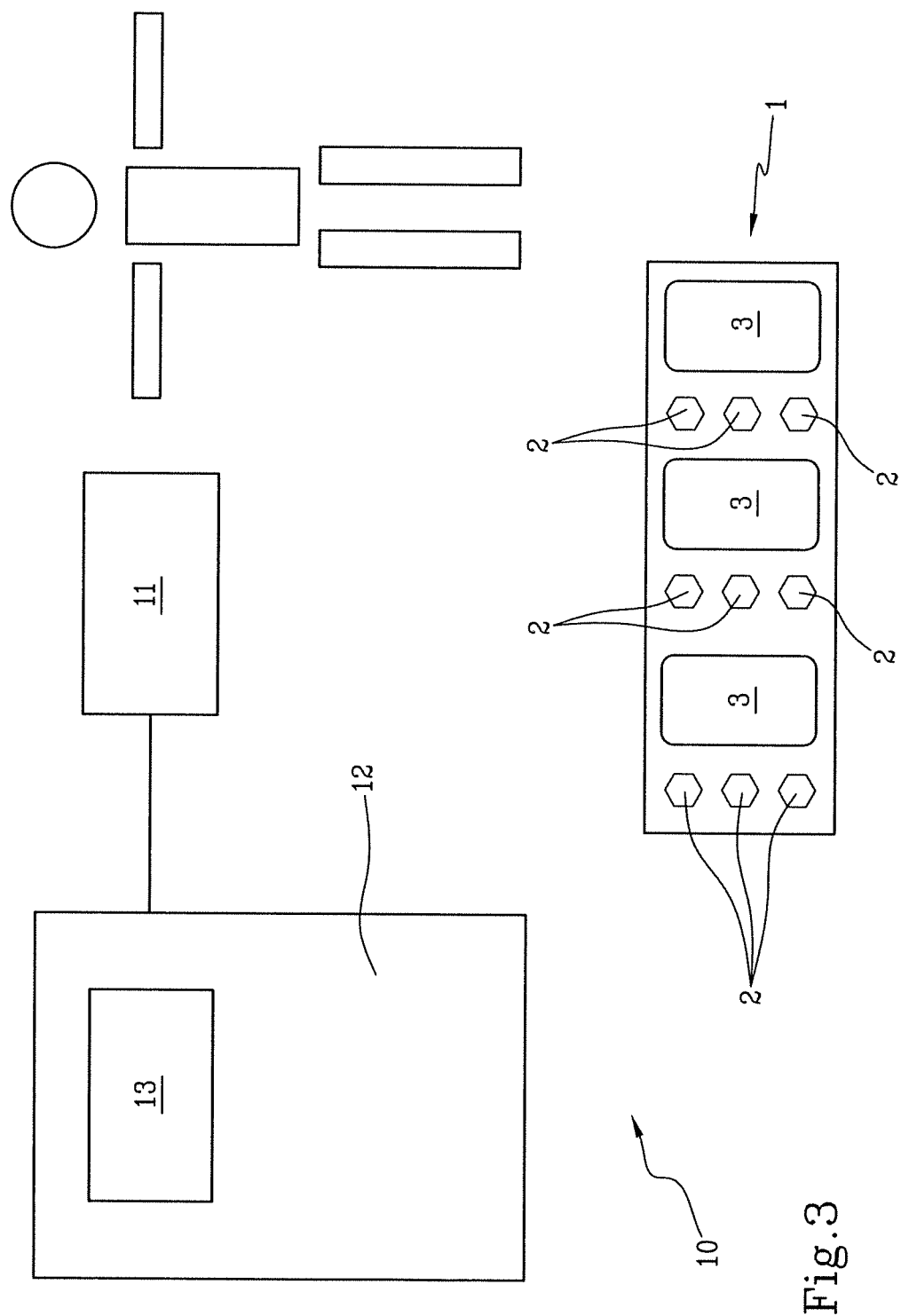
FIG. 3 is a schematic representation of a machine for interactive cerebral and bodily navigation comprising the control device of FIG. 2.

The invention also relates to a machine 10, displayed in FIG. 3, for magnetic cerebral or peripheral stimulation with cerebral and bodily navigation.

The machine 10 comprises a stimulation unit 11 configured for stimulating a patient. The stimulating unit 11 is thus configured to obtain the results to be sent to the machine 10.

The machine 10 comprises an acquisition unit 12 configured to acquire the results linked to the stimulation of the patient.

In other words, the acquisition unit 12 is configured to receive the results obtained and sent by the stimulation unit 11 following the stimulation of the patient.

The machine 10 also comprises a video unit 13 designed to display the results acquired from the acquisition unit 12 following the stimulation of the patient by the stimulation unit 11.

The machine 10 also comprises a control device 1 as described above (in the accompanying drawing, the machine 10 comprises the control device 1 according to the embodiment of FIG. 2).

According to the embodiment of FIG. 3, the control device 1 is of the wireless type but it can also be connected to the machine 10 by cable or be integrated in the machine 10.

Preferably, in an embodiment not illustrated, the touch screen 3 of the control device 1 comprises video unit 13 of the machine 10.

In other words, the control device 1 makes it possible to control the displaying of the results only from the touch screen 3 without requiring a screen 13 separate from it.

In this way, the operator or the doctor are able to completely control the functions to activate from the control device 1 without having to look away from the diagrams 6 of the results.

The control device 1 and the machine 10 are able to overcome the drawbacks of the prior art.

Advantageously, the control device 1 makes it possible to display the results obtained from the examination and to personalize the display.

Advantageously, the control device 1 allows the doctor or the operator to not be obliged to memorize the function of each individual key, thus facilitating the execution of the functions of the machine 10.

Advantageously, the control device 1 makes it possible to personalize the information which can be displayed by the touch screen 3 or the functions which must be activated by the keys 2, thus avoiding that possible software updates can modify the specific function of a key 2.

Advantageously, the control device 1 and the machine 10 make it possible to reduce the time for testing or setting up thanks to the presence of the touch screen 3 which allows timely operations and/or easy personalization of the control device 1.

As understood herein, a "computer-type system" comprises an operable system that has an input device for receiving data (data entry, pressure entry, wireless entry etc. in any form now known), an output device for outputting data in tangible form (e.g. printing or displaying on a computer screen), a permanent memory for storing data as well as computer code, and a microprocessor for executing computer code wherein said computer code resident in said permanent memory will physically cause said microprocessor to read-in data via said input device, process said data within said microprocessor and output said processed data via said output device. The memory may store transitory and non-transitory data.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related control devices and machines for interactive cerebral and bodily navigation with real-time anatomical display and control functions and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software (of all kinds), various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blue-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a website. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the word 'means' and 'for' in combination such as "means for" are intended to be interpreted under 35 USC 112 sixth paragraph/(f). Moreover, no limitations from the specification are intended to be read into any claims, unless those limitations are expressly included in the claims.

Having described at least one of the preferred embodiments of the present invention with reference to the accompanying drawings, it will be apparent to those skilled in the art that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A control device for a machine for magnetic cerebral or peripheral stimulation with cerebral and bodily navigation, comprising:
   a plurality of displaceable keys respectively associated with a plurality of functions of the machine, wherein each of the plurality of keys is configured for activating, upon being displaced by pressing by an operator of the machine, a respective one of the plurality of functions associated with that key;
   at least one touch screen configured for:
   displaying information relative to the various functions which is activated by the plurality of keys, and
   activating at least one further function of the machine associated with a respective icon displayed on the at least one touch screen by touching the at least one touch screen, and
   wherein the at least one touch screen is configured for displaying, for a physical examination in progress of a patient to assist in analysis of the patient, increased reality information 3D in real-time and also textual information on the respective function;
   wherein the control device is a wireless device physically separable from the machine, the control device configured to move around the patient to provide an image of the patient on the at least one touchscreen from a perspective of the operator with respect to the patient;
   a stimulation coil configured for stimulating the patient to provide at least a portion of the increased reality information 3D in real-time, the stimulation coil positioned on the control device, the stimulation coil configured to move with the control device to stimulate the patient also from the perspective of the operator with respect to the patient; and
   wherein both the image of the patient and the increased reality information 3D in real-time caused by the stimulating are displayed on the at least one touch screen from the perspective of the operator with respect to the patient.

2. The control device according to claim 1, wherein:
the at least one touch screen is configured for associating the functions of the machine to the respective key.

3. The control device according to claim 1, wherein:
the at least one touch screen is configured for personalizing a display of a result of the examination in progress.

4. The control device according to claim 1, wherein the at least one touch screen includes a plurality of touch screens with each of the plurality of touch screens being associated with at least one of the plurality of keys.

5. The control device according to claim 4, wherein:
the each of the plurality of touch screens being configured for displaying a respective result of an examination in progress, the each of the plurality of touch screens being associated with respective keys of the plurality of keys which are configured for executing the various functions of the machine associated with the respective result.

6. AThe machine for magnetic cerebral or peripheral stimulation with cerebral and bodily navigation comprising:
an acquisition unit configured for acquiring results linked to the stimulation of the patient;
a video unit for displaying the results; and
the control device according to claim 1.

7. The machine according to claim 6, wherein:
the at least one touch screen comprises the video unit.

* * * * *